US008061069B1

(12) United States Patent
Joseph

(10) Patent No.: US 8,061,069 B1
(45) Date of Patent: Nov. 22, 2011

(54) IDENTIFICATION BAND

(75) Inventor: Karen L. Joseph, Encino, CA (US)

(73) Assignee: St. John Companies, Inc., Valencia, CA (US)

( * ) Notice: Subject to any disclaimer, the term of this patent is extended or adjusted under 35 U.S.C. 154(b) by 125 days.

(21) Appl. No.: 12/260,274

(22) Filed: Oct. 29, 2008

(51) Int. Cl.

| | |
|---|---|
| ***A44C 5/00*** | (2006.01) |
| ***A61B 5/103*** | (2006.01) |
| ***A61B 5/117*** | (2006.01) |
| ***G09F 3/14*** | (2006.01) |
| ***G09F 3/20*** | (2006.01) |
| ***A42C 5/04*** | (2006.01) |

(52) U.S. Cl. .......... 40/633; 40/6; 40/665; 2/162; 283/81

(58) Field of Classification Search .................... 40/633, 40/6, 665; 2/162; 283/81
See application file for complete search history.

(56) References Cited

U.S. PATENT DOCUMENTS

| | | | | |
|---|---|---|---|---|
| 3,771,717 | A | 11/1973 | McDermott et al. | |
| 4,093,279 | A | 6/1978 | Verdesca et al. | |
| 4,314,415 | A | 2/1982 | De Woskin | |
| 4,612,718 | A | 9/1986 | Golub et al. | |
| 4,682,431 | A | 7/1987 | Kowalchuk | |
| 5,026,084 | A | 6/1991 | Pasfield | |
| 5,653,472 | A | 8/1997 | Huddleston et al. | |
| 5,758,443 | A | 6/1998 | Pedrazzini | |
| 5,933,993 | A | 8/1999 | Riley | |
| 6,000,160 | A | 12/1999 | Riley | |
| 6,016,618 | A * | 1/2000 | Attia et al. | 40/633 |
| 6,058,637 | A * | 5/2000 | Duncan | 40/633 |
| 6,067,739 | A | 5/2000 | Riley | |
| 6,438,881 | B1 | 8/2002 | Riley | |
| 6,510,634 | B1 | 1/2003 | Riley | |
| 6,517,921 | B2 * | 2/2003 | Ulrich et al. | 428/40.1 |
| 6,641,048 | B1 * | 11/2003 | Schintz et al. | 235/487 |
| 6,685,228 | B2 | 2/2004 | Riley | |
| 6,836,215 | B1 | 12/2004 | Laurash et al. | |
| 6,863,311 | B2 | 3/2005 | Riley | |

(Continued)

FOREIGN PATENT DOCUMENTS

WO WO9205036 A1 4/1992

*Primary Examiner* — Joanne Silbermann
*Assistant Examiner* — Syed A Islam
(74) *Attorney, Agent, or Firm* — Robert A. Schroeder; Sheldon Mak & Anderson PC

(57) ABSTRACT

A fabrication sheet is appropriately dimensioned and otherwise suitable for use with a printer. A symmetrical, removable and foldable identification band is included in the fabrication sheet. The fabrication sheet includes a rectangular backing sheet, covered by a working sheet, which may be made of imprintable woven polyester. The backing and working sheets are secured to each other by a releasable adhesive and have a combined thickness and flexibility that permits them to pass through a printer without difficulty. The working sheet is die-cut to define the outline of the band configured in such a way that it includes a strap portion and a tag portion. The tag portion is positioned at one end of and extends from the strap portion. The tag portion of the unfolded band includes wing sections extending outwardly, one from each side of the strap portion. The tag portion of the working sheet may include a generally rectangular patch of a different material that better accepts and holds a printed image. The working sheet includes two parallel linear series of spaced-apart insertion areas through which a fastener, such as a snap-on clasp, can be inserted to secure the band in a looped configuration. A perforation line or score line may be formed along the center axis of the band to facilitate folding.

11 Claims, 3 Drawing Sheets

U.S. PATENT DOCUMENTS

| | | | | |
|---|---|---|---|---|
| 7,017,293 | B2 | 3/2006 | Riley | |
| 7,017,294 | B2 | 3/2006 | Riley | |
| 7,047,682 | B2 | 5/2006 | Riley | |
| 7,137,216 | B2 | 11/2006 | Ali et al. | |
| 7,197,842 | B2 * | 4/2007 | Ali | 40/633 |
| 7,222,448 | B2 | 5/2007 | Riley | |
| 7,325,347 | B2 | 2/2008 | Riley | |
| 7,386,949 | B2 | 6/2008 | Riley | |
| 7,461,473 | B2 | 12/2008 | Riley | |
| 7,631,449 | B2 * | 12/2009 | McDermott et al. | 40/633 |
| 2003/0016122 | A1 * | 1/2003 | Petrick | 340/10.41 |
| 2004/0237367 | A1 * | 12/2004 | Ali | 40/633 |
| 2005/0260309 | A1 | 11/2005 | Hagemeyer et al. | |
| 2005/0279001 | A1 | 12/2005 | Riley | |
| 2005/0285385 | A1 | 12/2005 | Bova et al. | |
| 2006/0005441 | A1 | 1/2006 | Riley et al. | |
| 2006/0026015 | A1 | 2/2006 | Roberts, Jr. et al. | |
| 2006/0059753 | A1 | 3/2006 | Riley et al. | |
| 2006/0059754 | A1 | 3/2006 | Riley | |
| 2006/0113788 | A1 | 6/2006 | Riley | |
| 2006/0168861 | A1 | 8/2006 | Riley | |
| 2006/0218837 | A1 | 10/2006 | Riley | |
| 2006/0236578 | A1 * | 10/2006 | Saint et al. | 40/633 |
| 2007/0089342 | A1 | 4/2007 | Jain et al. | |
| 2007/0120358 | A1 | 5/2007 | Waggoner et al. | |
| 2007/0220796 | A1 | 9/2007 | Riley et al. | |
| 2007/0243361 | A1 | 10/2007 | Riley et al. | |
| 2007/0257118 | A1 | 11/2007 | Riley et al. | |
| 2008/0028655 | A1 | 2/2008 | Riley | |
| 2008/0098635 | A1 | 5/2008 | Jain et al. | |
| 2008/0098636 | A1 | 5/2008 | Greer | |
| 2008/0109937 | A1 | 5/2008 | Greer | |
| 2008/0110069 | A1 * | 5/2008 | McDermott et al. | 40/633 |

* cited by examiner

IDENTIFICATION BAND

FIELD OF THE INVENTION

The invention relates to identification bands of the type commonly secured to the wrist or ankle of a person or the leg of an animal. The invention also relates to printable fabrication sheets from which such bands can be made.

BACKGROUND OF THE INVENTION

It has become a common practice to attach a band to the wrist or ankle of a person or the leg of an animal for identification purposes. When used by a hospital, for example, the band can carry such information as a patient's name, number, medication requirements and instructions such as "do not recessitate". Information carried on the identification band is useful for correlating patients with medications, specimens and therapeutic treatments. Often information is recorded on the band in the form of a machine readable bar code that is integrated with a computerized patient information data system. Medical uses of identification bands are discussed in U.S. Patent Publication No. 2006/0236578. Similar identification bands can be attached to animals at veterinary and other animal handling facilities. In addition, identification bands are also used at sporting and entertainment events and in other environments.

In a hospital setting, by way of example, an identification band is typically prepared and printed at the time a patient is admitted in accordance with the established procedures of a particular facility. It is desirable to enter information regarding the patient only once, thereby permitting a single information input to be used to generate various forms, file labels, medication and specimen labels, and an identification band. This integrated data entry procedure not only saves time and reduces costs, but also reduces the potential for mistakes and inconsistencies.

It is, therefore, highly desirable that a wrist band or a fabrication sheet from which a wrist band is to be separated be printed at the same time and place that accompanying records and other materials are printed. The wrist band or fabrication sheet should be capable of passing through and being printed on by a printer of the type commonly used as a PC peripheral, e.g., an ink jet or laser jet printer that accepts ordinary paper sheets. The fabrication sheet should be of a size, shape, flexibility and thickness that permits this use without difficulty. It should not irritate the skin of the wearer and should be comfortable when in use. It should be of readily printable material and should retain the printed image without smudging or otherwise deteriorating.

There is, however, a problem that can arise in this regard because the identification band should also be sufficiently durable, tear-resistant, stain-resistant and cleanable to permit it to last throughout a patient's hospital stay, for example. It should not be easily removed inadvertently and should not be transferable from one patient to another. It is desirable that the band be adaptable for use with persons having a wide range of wrist, ankle sizes, (or leg sizes in the case of animals). It has proven difficult to achieve all these objectives. One reason for this problem is that the printer imposes limitations on the maximum thickness, rigidity and durability of the band.

There are two commonly used wrist band styles. One style, referred to here as the wrap-around style, consists of a band that is simply wrapped around the wrist or ankle of a person or the leg of an animal and secured by one or more plastic clasps. The desired information is printed on an exposed portion of the band itself. No part of the band carrying the information extends from or dangles from the portion of the band that wraps around the wrist, ankle or leg. The likelihood of part of the band being caught, damaged or inadvertently removed is thus minimized.

A second style, referred to here as the strap-and-tag style, uses a relatively thin strap that wraps around the wrist, ankle or leg, with a wider tag attached to one end of the strap. The tag is secured at only one end and is thus more easily manipulated to be read or scanned. This strap-and-tag style band provides a larger information field, while avoiding the discomfort and skin irritation that might result from the use of a strap wide enough to carry the same amount of information. Ideally, an identification band is capable of being used in either way.

It is desirable that the band be constructed in such a manner that it can be secured to the wrist or ankle of a person or the leg of an animal by one or more non-reusable, non-transferable snap-on clasps that permit adjustment of the length of the band and can be color coded to convey information.

SUMMARY

One aspect of the invention is a fabrication sheet appropriately dimensioned and otherwise suitable for use with a printer. An identification band is included in the fabrication sheet and can be removed. The fabrication sheet includes a rectangular backing sheet, which may advantageously be to 70 pound weight paper covered by a working sheet, which may be made of imprintable woven polyester. The backing and working sheets are secured to each other by a releasable adhesive and have a combined thickness and flexibility that permits them to pass through a printer without difficulty. Preferably the combined thickness is about 11 mil or less and more preferably 8.8 mil or less. The working sheet preferably has a thickness of about 3 mil or less.

The working sheet is die-cut to define the outline of a removable and foldable identification band configured in such a way that it includes a strap portion and a tag portion. The tag portion is positioned at one end of and extends from the strap portion. The tag portion of the unfolded band includes wing sections extending outwardly, one from each side of the strap portion. The tag portion of the working sheet may include a generally rectangular patch of a different material that better accepts and holds a printed image.

The working sheet includes two parallel linear series of spaced-apart insertion areas through which a fastener, such as a snap-on clasp, can be inserted to secure the band in a looped configuration. The insertion areas are located so that those of one series align with those of the other series when the identification band is folded along its longitudinal center axis. The unfolded band is symmetrical about that axis. A perforation line or score line may be formed along the center axis to facilitate folding.

According to one aspect of the invention, the working sheet is further die-cut to define the outline of a tab portion that is part of the identification band. The tab portion extends from the end of the tag portion opposite the end thereof attached to the strap portion. The tab portion has at least two insertion areas located so that they are aligned with each other when the identification band is folded along its center axis.

According to another aspect of the invention, a symmetrical identification band, which can be removed from the fabrication sheet described above, includes a sheet, preferably imprintable woven polyester, folded along its longitudinal axis. When so folded, the sheet adheres to itself so as to form a band having twice the original thickness of the sheet, thereby providing additional strength, tear resistance and rigidity.

The identification band has a strap portion and a tag portion. The strap portion is elongated and the tag portion is wider and positioned at one end of the strap portion. A series of spaced-apart insertion areas extend along the strap portion. The strap portion, once removed from the fabrication sheet and folded over, has two side edges, one aligned with a side of the tag portion. It includes a wing section offset from the strap portion and extending outwardly away from the strap.

According to another aspect of the invention, the band can include at least one snap-on closure, which may be color coded, extending through two aligned insertion areas of the strap, thereby causing the identification band to form a loop and assume a configuration. The band may also include a tab portion extending from the tag portion and aligned with the strap portion, whereby the band can be secured in a wrap-around configuration by positioning a clasp to extend through insertion areas of the strap and the tab.

Another aspect of the invention that can be advantageous in some circumstances includes a window in the tag portion of the band covered by a patch. The patch is made of a material that is readily printable and retains the printed image. The rest of the band is made of a material selected for reasons of comfort, such as a woven polyester.

DRAWINGS

These and other features, aspects and advantages of the present invention will be better understood with reference to the following description, appended claims and accompanying drawings where:

DETAILED DESCRIPTION

The following discussion describes in detail embodiments of the invention and variations of those embodiments. This discussion should not be construed, however, as limiting the invention to those particular embodiments and variations. Practitioners skilled in the art will recognize numerous other embodiments as well that fall within the scope of the invention. The invention will be described here with reference to a fabrication sheet and identification band suitable for hospital/medical use, but it should be understood that the invention is broader and is not limited to that particular use.

Figure 1:
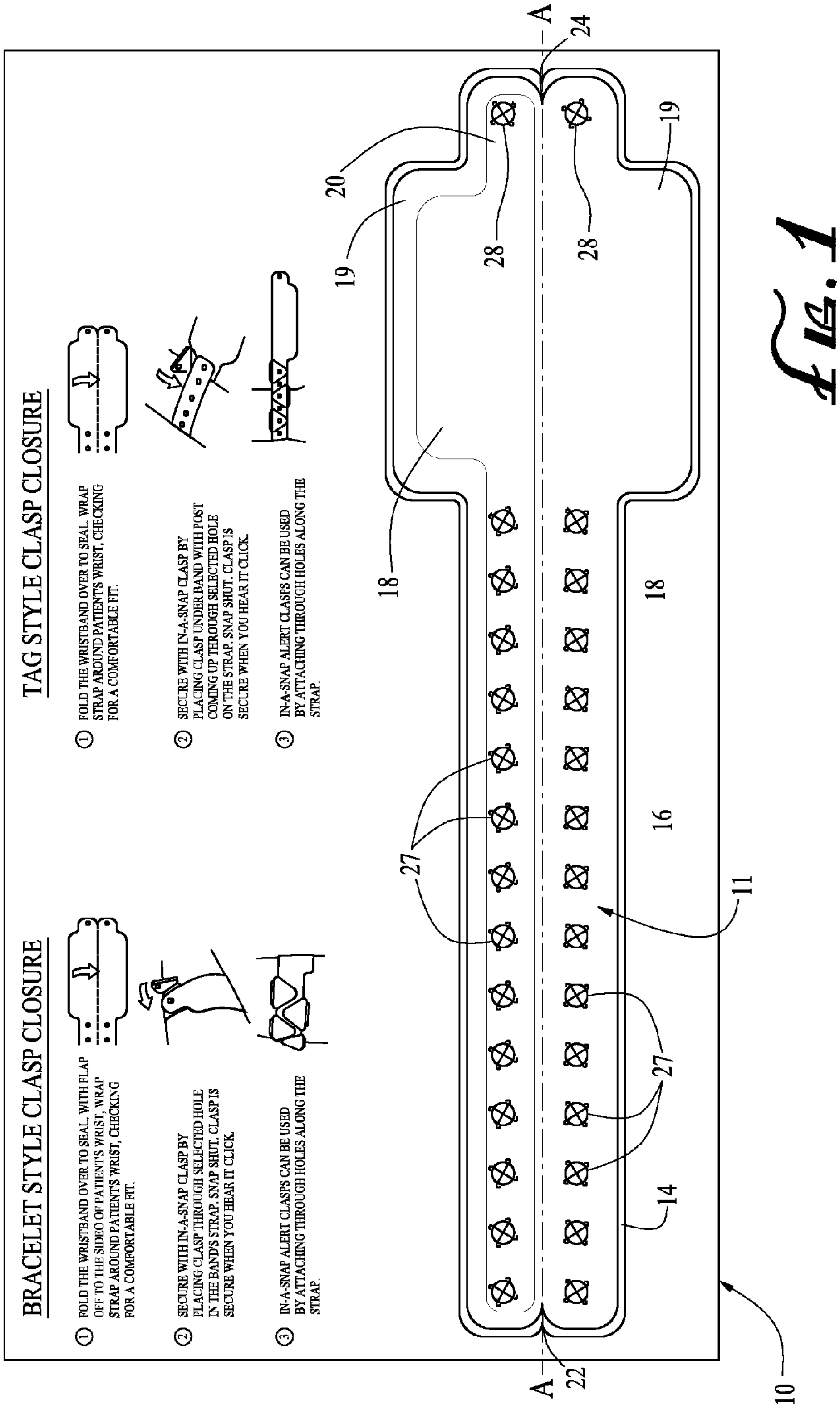
FIG. 1 is a top plan view of a fabrication sheet in accordance with the invention.

A fabrication sheet 10 from which an identification band 11 can be removed, shown in FIG. 1, includes two overlying laminations. The first lamination is a backing sheet or liner made of paper, preferably 70 pound weight. A working sheet of the same size and rectangular configuration overlies the backing. It is made of imprintable woven polyester. Opposing surfaces of the backing sheet and working sheet are secured to each other by a releasable adhesive. The fabrication sheet 10 is rectangular and dimensional so that it can readily be fed through a conventional printer. The fabrication sheet 10 is also of suitable thickness and flexibility to be used with a common printer, such as an ink jet printer or a laser jet printer, without jamming, tearing, delaminating or encountering other commonly experienced difficulties. Preferably, the thickness of the working sheet is 2.73 mil to 3.3 inch, more preferably about 3.0 mil or less. The thickness of the fabrication sheet 10 is preferably about 11 mil or less, most preferably 8.8 mil or less.

The working sheet, which is the top sheet shown in FIG. 1, is die-cut to define the outline of the identification band 11. In this preferred embodiment, there is a narrow peel away strip 14 surrounding the band 11, the peel-away strip being disposable to facilitate the removal of the band upon flexing. The peel away strip 14 can, however, be omitted, if desired. Portions of the working sheet not using the identification band 11 can be die-cut to form other removable elements such as labels for medicine or specimen containers.

The band 11 includes an elongated, generally rectangular strap portion 16 and a wider, generally rectangular tag portion 18. The tag portion 18 is positioned at and extends from one end of the strap portion 16 and is centered with respect to the strap portion, such that the tag portion and the strap portion have a common longitudinal center axis A-A. The tag portion 18, as compared to the strap portion 16, more closely approximates a square. The tag portion 18 forms two wings 19 extending outwardly beyond the sides of the strap portion 16.

Extending from the end of the tag portion 18 opposite the strap portion 16 is a small, generally rectangular tab portion 20 that is aligned with and centered with respect to the longitudinal center axis A-A of the strap portion and the tag portion. In this preferred embodiment the tab portion 20 has the same width as the strap portion 16.

All corners formed by the outline of the fabrication sheet 10 are rounded. There is a rounded indentation 22 at the end of the strap portion opposite the tab portion 18 that is aligned with the longitudinal center axis A-A and there is a similar rounded indentation 24 at the center of the tab portion 20 at the opposite end of the band 11. These indentations give the band 11 rounded corners when removed from the fabrication sheet 10 and folded. Rounded corners are preferred because they tend to prevent tearing or delamination and reduce any tendency of bacteria or other foreign matter to accumulate as a result of delaminination at the corners. Rounded corners are also more comfortable for the wearer, having less potential for causing skin irritation.

The center axis A-A divides the strap portion into similar, complementary upper and lower halves, as shown in FIG. 1. A perforated fold-line extends along and coincides with the center axis A-A to facilitate folding, as explained below. There are two linear parallel rows of spaced-apart insertion areas 27, one extending longitudinally along each half of the strap portion 16. In addition, the tab portion 20 has two insertion areas 28, one aligned with each row of insertion areas 27 on the strap portion 16. If desired, the tab portion 20 can be elongated to accommodate multiple clasps insertion areas arranged in parallel rows, as on the strap portion 16. Each insertion area 27, 28 is formed by two perpendicular intersecting die-cuts or score-lines in the working sheet forming a small X-shaped pattern, thus permitting a projecting leg of a snap-on clasp to pass easily through the insertion area, as explained below. Score lines, if used, deform and weaken but do not penetrate the working sheet in a known manner, which is advantageous in many environments. They avoid any tendency to allow water to seep in and bateria to grow and avoid any tendency to collect other contaminants. There are, however, other ways within the scope of the invention of forming the insertion areas which may, for example, be die-cut circles that define round holes. The insertion areas 27 may be marked with an "X" or other symbol.

Before folding, band 11 is symmetrical about its longitudinal center axis A-A. It will be appreciated that the proportions and configuration of the band 11 may be varied, depending upon the needs of a particular user. A single band per fabrication sheet will most commonly be preferred because each patient usually requires only one band. There are, however, situations in which it is desirable to have more than one band on a sheet so that multiple bands can be printed on one pass through the printer. For example, it may be desirable to print three bands on one sheet for a mother, father and infant.

When a person is admitted to a medical facility or other facility or area at which identification bands are used, information is usually entered into a computerized database, which may include, for example, a patient's name, a number assigned to the patient, the date of admission, the name of the responsible physician and such other desired information. Once this information has been entered, various labels and forms are printed. As part of the same procedure the fabrication sheet 10 is passed through a printer and information is printed on the tab portion 18. Additional information may, if desired, be printed on the strap portion 16 of the band 11. If desired, other portions of the working sheet may be die-cut to form other removable elements such as labels for medicine or specimen containers.

Figure 2:
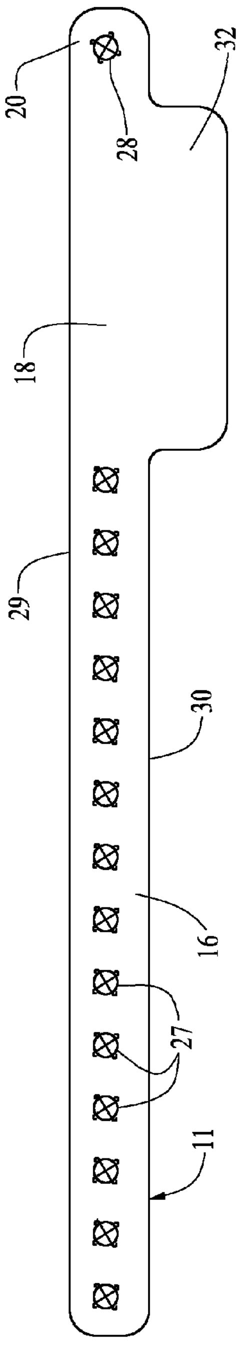
FIG. 2 is a top plan view of a folded identification band, made from the fabrication sheet of FIG. 1, in accordance with the invention.

After the printing step has been completed, the identification band 11 is removed by peeling it away from the backing sheet and the narrow peel-away strip 14 extending along the periphery of the band is discarded. The band 11 is then folded along the perforated fold line that coincides with the center axis A-A. Once folded the band 11, shown in FIG. 2, has twice the thickness of the working sheet, thus making it more durable, tear resistant and easier to handle. If, however, the working sheet had originally been of the double thickness obtained by folding, the fabrication sheet 10 would not readily passed through a printer.

The folded band 11 assumes an asymmetrical shape. One edge 29 forms a continuous straight line extending along the strap portion 16 the tag portion 18 and the tab portion 20. This side edge of the band corresponds to the longitudinal center axis A-A of the unfolded band. On the opposite side 30 of the strap portion 16, the generally rectangular and wider tag portion 18 extends beyond the side of the strap portion, providing a wing 32 and an enlarged field to contain printed information. The two rows of insertion areas 27 on the strap 16 align with and coincide with each other.

Figure 3:
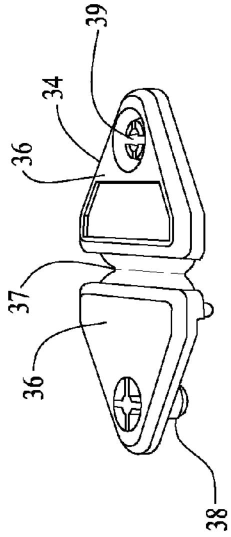
FIG. 3 is a perspective view of a snap-on clasp that can form part of the band shown in FIG. 2.

When the band 11 is put to use, it can be attached to, for example, the wrist or ankle of the wearer in either a wrap-around style or a strap-and-a-tag style. Either style makes use of one or more fasteners, preferably plastic snap-on clasps 34, as shown in FIG. 3. The clasps can be color coded to impart information about the patient and his or her treatment. Each clasp 34 is of a known design and includes two preferably triangular panels 36 foldably joined along a hinge line 37. One panel 36 carries a perpendicularly extending leg 38, whereas the other panel contains an opposing recess 39 in which the projecting end of the leg can be received. Once the clasp has been closed by folding, the leg end 38 is forced resiliently into the recess 39 and cannot be readily removed without breaking the leg 38 so that the clasp cannot be reused. This non-reusable clasp design makes it more difficult to transfer the band 11 from one weaver to another.

Clasps can be color coded to provide information, in a known manner. If the tab portion 20 includes only a single insertion point, only one clasp 34 can serve a securement function, but additional clasps can be attached at other insertion points on the strap 16 for coding/information purposes.

Figure 4:
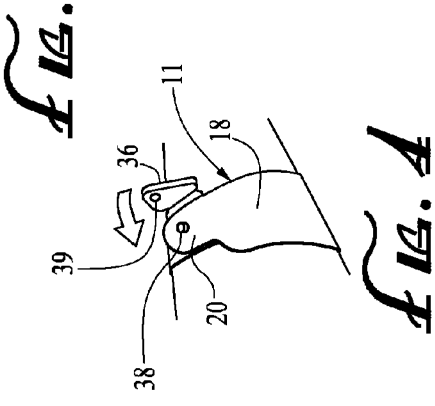
FIG. 4 is a perspective view of the band used in a wrap-around configuration (the clasp being open)
Figure 6:
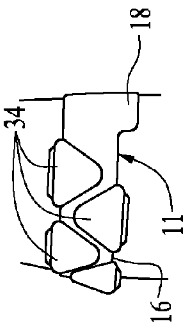
FIG. 6 is another perspective view of the band shown above used in a wrap-around configuration.

When the band 11 is used in the wrap-around style, as shown in FIGS. 4 and 6, the insertion area 28 of the tab 20 is aligned with one of the insertion areas 27 of the strap 16, the effective strap length being chosen to provide a loop of appropriate size for the wearer's writ or ankle. The unused portion of the strap 16 is positioned inside the loop thus formed and need not be cut off.

Figure 5:
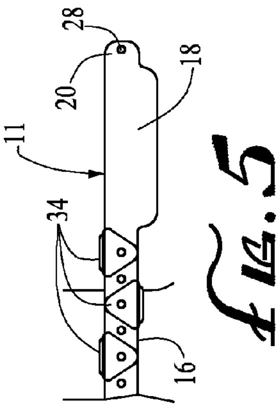
FIG. 5 is a perspective view of the band used in a strap-and-a-tag configuration.

Alternatively, the same band 11 may be secured to the wearer in the strap-and-tag style, as shown in FIG. 5. In this case, only the strap 16 is looped about the wearer's wrist or ankle and at least one pair of strap insertion areas 27 are caused to be aligned. A clasp 34 is then inserted and the band is secured with the tag 18 depending from the strap 16, but not forming part of the loop, as shown in FIG. 5. When the band 11 is worn in this manner, the tab 20 is not used. If desired, the tab 20 may be omitted when the band 11 is to be used only in the strap-and-a-tag style.

It is preferable that the clasp panels 36 each have a triangular configuration, as shown in FIGS. 5 and 6, to permit the clasps 34 to be interleaved and alternately secured from opposite sides of the strap 16, as shown in FIGS. 5 and 6. If desired, the tab 20 may be made longer so as to include parallel rows of insertion areas, in the manner of the strap portion. This permits multiple triangular clasps 34 to be used with the tab portion 20 instead of relying on a single clasp 34 to secure the band 11.

Figure 7:
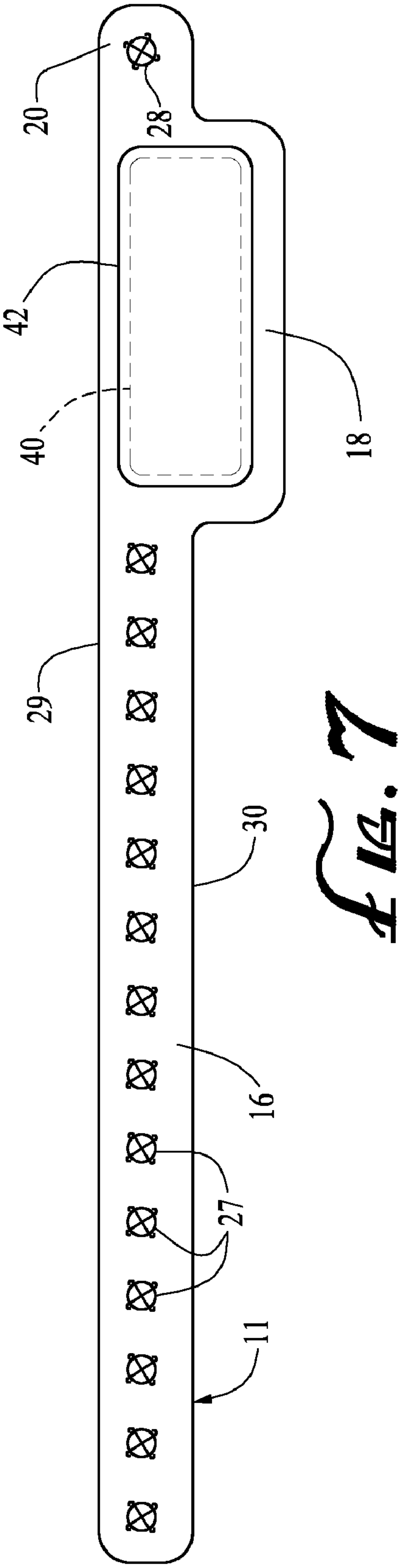
FIG. 7 is similar to FIG. 2, but shows an alternative embodiment of the invention.

A second embodiment of the invention, shown in FIG. 7, utilizes a similar band 11 in which a rectangular window 40 with rounded corners is cut from the tag portion 20 corresponding to the tab portions 20 of the strap 16 on one side of the center line A-A. The window 40 is then covered by patch 42 which is of a different material from the rest of the band 11. A band having a window 40 and a patch 42 on only one side is shown in FIG. 7, but patches can be provided on both sides of the band 11 if desired. The patch 42 is slightly larger than the window 40, so that it overlaps the other material of the band around the entire periphery of the window and is secured by adhesive. The patch 42 is a printable, durable non-woven polyester, preferably 3-4 mil thick.

It is desirable to use the patch 42 to provide the print field in some situations because the woven polyester of the band is selected for reasons of its softness and comfort. The woven material is not, however, ideal for printing and may not retain ink as well as desired, particularly under adverse conditions. The patch 42 provides superior printing surface and retains ink better over time. Factors that determine whether a patch should be included include the environment in which the band will be used, the time period over the band will be used and the size of the print.

Having thus described the invention, it should be apparent that numerous structural modifications and adaptations may be resorted to without departing from the scope and of the instant invention as set forth and as defined by the following claims.

I claim:

1. An asymmetrical identification band comprising:

a sheet folded along a longitudinal center axis and adhered to itself so as to form a band having twice the thickness of the sheet;

the band having a strap portion and a tag portion, the strap portion being elongated, and the tab tag portion extending from one end of the strap portion and having two parallel sides, one side being aligned with a side of the strap portion and the other being offset from the strap portion to provide a wing section that extends outwardly beyond the width of the strap portion; and the band further having a series of spaced-apart clasp insertion areas extending along the strap portion; and the band further comprising a window formed on the wing section and a patch of more readily printable material that overlies the window, the rest of the sheet being formed of woven polyester.

2. The band of claim 1 further comprising a snap-on clasp that extends through two of said insertion area of the strap portion, thereby causing the band to assume a loop and to have a strap-and-tag configuration.

3. The band of claim 1 further comprising a tab portion extending from the tag portion and aligned with the strap portion, whereby the band can be caused to have a strap-and-tag configuration by positioning a snap-on clasp to extend through two aligned insertion areas of said strap, and the band can alternatively be caused to have a wrap-around configuration by positioning a snap-on clasp to extend through an insertion area of the strap portion and an aligned insertion area of the tab portion.

4. The band of claim 1, wherein the sheet is made of imprintable woven polyester.

5. The band of claim 1, wherein the sheet is made of imprintable woven polyester and has a thickness of about 2.7-3.7 mil.

6. The band of claim 1 further comprising a line of perforations extending along its longitudinal center axis.

7. An asymmetrical identification band comprising:

a sheet folded along a longitudinal center axis and adhered to itself so as to form a band having twice the thickness of the sheet;

the band having a strap portion and a tag portion, the strap portion being elongated, the tag portion being wider than the strap portion and extending from one end of the strap portion;

the band further having a series of spaced-apart clasp insertion areas extending along the strap portion; and the band further comprising a window formed on the wing section and a patch of more readily printable material that overlies the window, the rest of the sheet being formed of woven polyester.

8. The band of claim 7 further comprising a snap-on clasp that extends through two of said insertion areas of the strap portion, thereby causing the band to assume a loop and to have a strap-and-tag configuration.

9. The band of claim 7 further comprising a tab portion extending from the tag portion and aligned with the strap portion, whereby the band can be caused to have a strap-and-tag configuration by positioning a snap-on clasp to extend through two aligned insertion areas of said strap, and the band can alternatively be caused to have a wrap-around configuration by positioning a snap-on clasp to extend through an insertion area of the strap portion and an aligned insertion area of the tab portion.

10. The band of claim 7, wherein the sheet has a thickness of about 2.7-3.7 mil.

11. A rectangular fabrication sheet having a thickness of no more than about 8.8 mil and suitable for use with a printer from which an identification band can be removed, the fabrication sheet comprising:

a backing sheet of paper overlying a working sheet of imprintable woven polyester, the sheets being secured to each other by a releasable adhesive, the thickness of the working sheet being between about 2.7 and 3.3 mil;

the working sheet being die-cut so as to define the outline of an unfolded identification band that is symmetrical with respect to a longitudinal center axis and configured in such a manner that it includes an elongated, generally rectangular strap portion and a tag portion of greater width than the strap portion;

the tag portion being positioned at and extending from an end of the strap portion and having two wing sections, one extending outwardly beyond each side of the strap portion;

the working sheet being further die-cut so that all corners of the defined identification band are rounded, the fabrication sheet being still further die-cut to define a rounded indentation at the end of the strap portion opposite the tab portion that is aligned with the center axis;

the working sheet including two parallel linear series of spaced-apart clasp insertion areas in the strap portion through which one or more non-reusable clasps can be inserted to secure the band in a looped configuration, the insertion areas being located so that those of one series align with those of the other series when the identification band is folded along its longitudinal center axis; and the working sheet being further die-cut so as to define the outline of a tab portion that forms part of the identification band, the tab portion extending from an end of the tag portion opposite an end thereof that is attached to the strap portion, said tab portion having at least one insertion area.

* * * * *